(12) United States Patent
Hayashi et al.

(10) Patent No.: US 7,291,594 B2
(45) Date of Patent: Nov. 6, 2007

(54) GLP-1 DERIVATIVE AND PREPARATION THEREOF ABSORBABLE VIA MUCOUS MEMBRANE

(75) Inventors: Yuji Hayashi, Nagoya (JP); Mitsuhiro Makino, Nagoya (JP); Toshiyuki Kouzaki, Nagoya (JP); Motohiro Takeda, Nagoya (JP); Takahito Jomori, Nagoya (JP)

(73) Assignee: Sanwa Kagaku Kenkyusho Co., Ltd., Nagoya-Shi (JP)

( * ) Notice: Subject to any disclaimer, the term of this patent is extended or adjusted under 35 U.S.C. 154(b) by 0 days.

(21) Appl. No.: 10/530,125

(22) PCT Filed: Oct. 10, 2003

(86) PCT No.: PCT/JP03/13020

§ 371 (c)(1),
(2), (4) Date: Oct. 27, 2005

(87) PCT Pub. No.: WO2004/037859

PCT Pub. Date: May 6, 2004

(65) Prior Publication Data

US 2006/0194720 A1    Aug. 31, 2006

(30) Foreign Application Priority Data

Oct. 11, 2002   (JP)   ............................. 2002-299283

(51) Int. Cl.
*A61K 38/26* (2006.01)
*C07K 14/605* (2006.01)

(52) U.S. Cl. ...................... 514/12; 514/866; 530/308; 530/324

(58) Field of Classification Search .................... None
See application file for complete search history.

(56) References Cited

U.S. PATENT DOCUMENTS

| 6,528,486 | B1 | 3/2003 | Larsen et al. |
| 6,903,186 | B1 * | 6/2005 | Dong .......................... 530/324 |
| 2003/0199672 | A1 * | 10/2003 | Knudsen et al. ............. 530/324 |

FOREIGN PATENT DOCUMENTS

| CA | 2 321 026 | 9/1999 |
| EP | 0 978 565 A1 | 2/2000 |
| EP | 1 076 066 | 2/2001 |
| EP | 1 329 458 | 7/2003 |
| JP | 1996-A-027018 | 1/1996 |
| JP | 2002-509082 | 3/2002 |
| JP | 2002-512175 | 4/2002 |
| JP | 2003-505347 | 2/2003 |
| WO | 99/43706 | 9/1999 |
| WO | 99/46283 A1 | 9/1999 |
| WO | 01/04156 A1 | 1/2001 |

OTHER PUBLICATIONS

C.F. Deacon et al., "Dipeptidyl peptidase IV resistant analogues of glucagon-like peptide-1 which have extended metabolic stability and improved biological activity", Diabetologia (1998) 41:271-278.

Q. Xiao et al., "Biological Activities of Glucagon-Like Peptide-1 Analogues in Vitro and in Vivo", Biochemistry 2001, 40: 2860-2869.

C. Mark B. Edwards et al., "Exendin-4 reduces fasting and postprandial glucose and decreases energy intake in healthy volunteers", Am J Physiol Endocrinol Metab, 281: E155-E161, 2001.

Mark K. Gutniak, MD, PHD et al., "GLP-1 Tablet in Type 2 Diabetes in Fasting and Postprandial Conditions", Diabetes Care, vol. 20, No. 12, Dec. 1997, pps. 1874-1879.

* cited by examiner

*Primary Examiner*—Anish Gupta
*Assistant Examiner*—Julie Ha
(74) *Attorney, Agent, or Firm*—Burr & Brown

(57) ABSTRACT

A GLP-1 derivative is provided including an amino acid sequence of GLP-1 (7-35) having deletion, substitution and/or addition of one or more amino acids and having Waa-(Xaa)n-Yaa (in which Waa is Arg or Lys, Xaa is Arg or Lys, n is an integer of 0 to 14, and Yaa is Arg, Arg-NH$_2$, Lys, Lys-NH$_2$ or Hse) added to the C-terminus of the peptide having a GLP-1 activity. These derivatives are highly absorbable via a mucous membrane. The GLP-1 derivative can be conferred with resistance to dipeptidyl peptidase IV by substituting amino acid 8 in its GLP-1 amino acid sequence with Ser, or with resistance to trypsin by substituting amino acids 26 and 34 with Gln and Asn, respectively.

The absorption efficiency of the GLP-1 derivatives via mucous membranes can be further improved by preparing a composition using a charge-regulated fat emulsion regulated to be negatively charged thereon.

16 Claims, No Drawings

GLP-1 DERIVATIVE AND PREPARATION THEREOF ABSORBABLE VIA MUCOUS MEMBRANE

CROSS REFERENCE TO RELATED APPLICATION

This application is a National Phase of International Application No. PCT/JP2003/013020 having an international filing date of Oct. 10, 2003, published in Japanese on May 6, 2004, which claims the benefit of Japanese Application 2002-299283, filed Oct. 11, 2002, the entirety of which is incorporated herein by reference.

TECHNICAL FIELD

The present invention relates to novel human glucagon-like peptide-1 (GLP-1) derivatives absorbed highly via a mucous membrane in the oral cavity, lung, nose or intestines, production thereof and a method of using the same.

BACKGROUND ART

GLP-1 (Glucagon-Like Peptide-1) is known as an incretin hormone which is secreted from digestive tracts upon ingestion of food to act on the pancreas and stimulate insulin secretion. As a hormone exhibiting a similar action, there is GIP (Gastric Inhibitory Polypeptide or Glucose-dependent Insulinotropic Polypeptide). This incretin effect is suggested to be absent or reduced inpatients with type 2 diabetes, compared with healthy persons, and this is considered as one of causes high blood glucose. For example, it is reported that inpatients with type 2 diabetes, blood GLP-1 level is lowered, while blood GIP level is normal. As a result of administering the incretin hormones to patients with type 2 diabetes, there is no difference upon the insulin secretion-stimulating activity of GLP-1 between the patients and healthy persons, while the insulin secretion-stimulating activity of GIP is significantly lower in the patients than healthy persons. Accordingly, the response of the patients with diabetes to GLP-1 is maintained; thus, a GLP-1 preparation compensating for its shortage can be expected to serve as a medicine for treatment of diabetes.

The action of GLP-1 on insulin secretion is characterized by glucose level dependent that GLP-1 does not stimulate insulin secretion in the blood glucose level of 110 mg/dL or less. That is, Administration of GLP-1 has clinical advantages that lower possibility of hypoglycemia, and suppress the excessive insulin secretion so that the exhaustion of the pancreas is is prevented. While A sulfonylurea, used mainly in treatment of type 2 diabetes, closes ATP-sensitive $K^+$ channels continuously to promote insulin secretion it causes low blood glucose, exhaustion of the pancreas by excessive stimulation of β cells, and secondary failure in administration for a long period of time. Accordingly, the pharmacological characteristics of GLP-1 are very useful and different from those of the conventional medicine for diabetes.

GLP-1 also have the following characteristics: suppression of glucagon secretion, delay of gastric emptying, suppression of stomach acid secretin, action on the brain to suppress appetite, promotion of insulin synthesis in pancreatic β cells and proliferation of pancreatic β cells. Therefore, GLP-1 is considered not only effective for treatment of diabetes by antagonizing the cause of high blood glucose such as hyperglucagonemia in type 2 diabetes, but also effective for treatment of obesity.

However, as GLP-1 is the polypeptide made up of 30 or 31 amino acids, it is digested upon oral ingestion and decomposed by digestive enzyme in the digestive tract, and is thus not absorbed. The administration thereof by intravenous injection or subcutaneous injection of GLP-1 is attempted at present. Further, it is known that GLP-1 undergoes decomposition with dipeptidyl peptidase IV (DPPIV) present in blood or tissues so that the half-life thereof in the living body is as very short as 1 to 2 minutes, thus giving rise to an obstacle to clinical applications.

To solve these problems, some researches and developments have been made. It is attempted to develop, for example, its derivative having an amino acid sequence substituted at position 8 which is hardly degradable to attain a longer half-life (Diabetologia 41: 271-278 (1998) and Biochem 40: 2860-2869 (2001)) and a sustained-release injection showing sustained subcutaneous absorption. An injection of lizard-derived, synthetic Exendin-4 having a GLP-1 like agonistic activity and a long half-life in blood (Am J Physiol 281: E155-E161 (2001)) is also developed. However, an administration route other than via an injection is desired for wide application of GLP-1 as a medicine for diabetes and in consideration of patients' burden and convenience.

As an administration method not using an invasive means such as an injection or a preparation for oral administration, use of a preparation for absorption through mucous membranes in the lung, oral cavity, nasal cavity, vagina, eye, rectum and the like is available. But a peptide such as GLP-1 upon being administered alone, is poor in absorption via a mucous membrane. Accordingly, a polymer such as peptide is formulated together with an absorption promoter. To secure sustained absorption of chemicals, the preparation makes use of a water-soluble or water-swelling binder, and is formulated in the form of film adhering to the skin layer, buccal tablets, ointment or troche. Many absorption promoters or binders have been examined and found to be effective in facilitating administration of chemicals via mucous membranes. However, as the absorption rate, in terms of bioavailability, of GLP-1 in buccal tablets containing 400 μg GLP-1 through a mucous membrane in the human oral cavity reported by Gutniak et al. ("Diabetes Care" 20: 1874-1879 (1997)), even by using the prior art described above, is 7% of the absorption of its intravenous injection or 47% of the absorption of its subcutaneous injection, and its absorptivity is not sufficient.

Dipeptidyl peptidase IV is known as an enzyme degradating of GLP-1, which is widely distributed not only in the kidney, liver, small intestine, salivary gland and various connecting tissues, but also in body fluid such as blood, urine and saliva and in a mucous membrane in the nasal cavity, and also possibly in other mucous membrane tissues.

DISCLOSURE OF INVENTION

Absorption of GLP-1 via mucous membrane, as compared with absorption by an injection, is considerably ineffective due to low membrane permeability and degradation in absorption sites. Though the nasal administration of GLP-1 as such is not impossible a very large dose of GLP-1 is necessary for achieving a sufficient pharmacological effect. Accordingly, development of naturally occurring GLP-1 as a pharmaceutical preparation for nasal administration is unrealistic from the viewpoint of the production cost of GLP-1 peptide. For clinical application of GLP-1, it is necessary to develop GLP-1 derivatives whose absorptivity via mucous membranes is comparative to that of an injection. Accordingly, the present inventors anticipated novel GLP-1 derivatives with improved absorptivity via mucous membranes, and made extensive studies to provide a preparation for mucous membrane administration as a substitute for an injection.

As a result, the inventors arrived at a novel idea that the absorption of GLP-1 via mucous membranes can be increased by adding positively charged arginine or lysine. In addition, they anticipated addition of several residues of arginine and/lysine to the C-terminus thereof while the N-terminus important for expressing the activity was kept intact, to obtain GLP-1 derivatives described below. For further increasing absorptivity via mucous membranes, a charge-regulated fat emulsion having a surface regulated to be negatively charged was used to devise a GLP-1 preparation with significant improvement in mucous membrane absorption.

That is, the GLP-1 derivative of the present invention is a peptide comprising an amino acid sequence of GLP-1 (7-35) having deletion, substitution and/or addition of one or a few amino acids and having a GLP-1 activity with Waa-(Xaa)n-Yaa (in which Waa is Arg or Lys, Xaa is Arg or Lys, n is an integer of 0 to 14, and Yaa is Arg, Arg-$NH_2$, Lys, Lys-$NH_2$ or Hse) on its C-terminus of the peptide. As described above, a novel GLP-1 derivative showing high absorption via mucous membranes, that is, high bioavailability via mucous membranes, can be provided by adding several residues of arginine and/or lysine to the C-terminus thereof.

To confer resistance to dipeptidyl peptidase IV, amino acid in position 8 of the GLP-1 derivative of the present invention is preferably serine. Such peptide is represented by the general formula: [$Ser^8$]-GLP-1 (7-35)-Waa-(Xaa)n-Yaa (in which Waa is Arg or Lys, Xaa is Arg or Lys, n is an integer of 0 to 14, and Yaa is Arg, Arg-$NH_2$, Lys, Lys-$NH_2$ or Hse).

The GLP-1 derivative of the present invention can be endowed with trypsin resistance by substituting lysine at position 26 with glutamine and lysine at position 34 with asparagine. Such peptide is represented by the general formula: [$Gln^{26}$, $Asn^{34}$]-GLP-1(7-35)-Waa-(Xaa)n-Yaa (in which Waa is Arg or Lys, Xaa is Arg or Lys, n is an integer of 0 to 14, and Yaa is Arg, Arg-$NH_2$, Lys, Lys-$NH_2$ or Hse).

As a matter of course, these dipeptidyl peptidase IV-resistant or trypsin-resistant GLP-1 derivatives can also have deletion, substitution and/or addition of one or more amino acids in the amino acid sequence of GLP-1 (7-35).

In the GLP-1 derivatives of the present invention, n is preferably an integer of 1 to 9, more preferably an integer of 3 to 5.

The most preferable peptide among the GLP-1 derivatives of the present invention is represented by the general formula: [$Ser^8$, $Gln^{26}$, $Asn^{34}$]-GLP-1 (7-35)-(Arg)n-Yaa (in which n is an integer of 4 to 6, and Yaa is Arg or Arg-$NH_2$).

The efficiency of absorption of the GLP-1 derivative was examined by administering the GLP-1 derivative of the present invention into mice via the nose, and then measuring its blood glucose lowering activity and insulin secretion stimulating activity in the mice in a oral glucose tolerance test. As a result, the GLP-1 derivative showed a high blood glucose depressing action and insulin secretion promoting action, and the GLP-1 derivative of the invention in an amount of 1/10 relative to naturally occurring GLP-1 showed a similar effect to that of the naturally occurring GLP-1, and it is thus estimated that the absorption via the nasal mucous membrane is 10 times as high as that of the natural one.

For improving the efficiency of absorption of the GLP-1 derivative of the present invention, a charge-regulated fat emulsion described in JP-A8-27018 was used to make a preparation. That is, the present invention also provides a GLP-1 preparation comprising the fat emulsion regulated to be negatively charged thereon and the GLP-1 derivative of the present invention.

The charge-regulated fat emulsion is a fat emulsion regulated to be negatively charged thereon, which is considered to absorb a peptide and protein thereby improving the stability of the peptide and protein against enzymes, simultaneously enhancing its pharmacological effect and extending duration. The GLP-1 derivative of the present invention, on one hand, has positively charged residues of arginine or lysine added thereto, and thus easily adheres to the charge-regulated fat emulsion. Accordingly, it is estimated that the mucous membrane absorption of the GLP-1 derivative of the present invention is increased when its preparation is produced by using the charge-regulated fat emulsion. When the efficiency of absorption of the GLP-1 derivative was actually examined by administering the preparation containing the GLP-1 derivative used in combination with the charge-regulated fat emulsion to mice in a glucose tolerant test and then measuring its blood glucose lowering activity in the mice, the GLP-1 derivative of the present invention in an amount of 1/30 relative to the naturally occurring GLP-1 exhibited an effect similar to the natural one. That is, it is considered that the absorption of the GLP-1 derivative of the present invention via the nasal mucous membrane, when used in combination with the charge-regulated fat emulsion, is 30 times as high as that of the naturally occurring GLP-1.

As described above, the GLP-1 derivative of the present invention is the most suitable peptide for making a preparation having high absorptivity via mucous membranes, in particular, via the nasal mucous membrane. The GLP-1 derivative of the present invention, upon substitution at position 8 with serine, is made hardly degradable with dipeptidyl peptidase IV occurring in blood and tissues, thus giving a GLP-1 derivative having a longer half-life in the living body. By conferring trypsin resistance as described above, the GLP-1 derivative can be protected against degradation with trypsin or trypsin-like enzymes and so on occurring in tissues, thus further improving bioavailability.

By combination with the charge-regulated fat emulsion, the GLP-1 derivative of the present invention can improve mucous membrane absorptivity to exhibit its effect in such a low dose as in an injection. That is, the present invention is to significantly improve the clinical applicability of a mucous membrane absorption-type GLP-1 preparation, which can be easily administered into patients without pain, to improve the quality of life of patients with diabetes and patients with obesity.

BEST MODE FOR CARRYING OUT THE INVENTION

Hereinafter, the present invention will be described in detail. GLP-1 (7-35) is a peptide having the following sequence: His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly (SEQ ID NO: 1). Herein, [$Ser^8$] means that amino acid at position 2 in this sequence, that is, Ala at position 8 is replaced by Ser, and [$Ser^8$] has the same meaning as 8S. Further, —$NH_2$ indicates that the sequence in question is amidated, and the GLP-1 derivative of the present invention can take a form amidated or not amidated at the C-terminus thereof.

The GLP-1 derivative of the present invention can be produced by chemical synthesis or genetic recombination techniques.

The principle of chemical synthesis of polypeptides is known in the technical field of the present invention. For this principle, reference can be made to the following general texts: Dugas H. and Penney C., "Bioorganic Chemistry" (1981) Springer-Verlag, New York, pp. 54-92; Merrifields J M, Chem. Soc., 85: 2149 (1962); and Stewart and Young, "Solid Phase Peptide Synthesis", items 24-66, Freeman (San Francisco, 1969). For example, 430A peptide synthesizer (PE-Applied Biosystems Inc., 850 Lincoln Center Drive, Foster City Calif. 94404) and a synthetic cycle supplied by PE-Applied Biosystems can be used to synthesize the peptide of the present invention by the solid phase method. Boc amino acids and other reagents can be purchased from PE-Applied Biosystems and other chemical suppliers.

Hereinafter, the method of producing the peptide of the present invention by genetic recombination techniques will be described in detail.

The DNA of GLP-1 is obtained by synthesis or by modifying DNA encoding a larger naturally occurring glucagon. A DNA sequence encoding a preproglucagon is shown by Lund et al. (Proc. Natl. Acad. Sci. USA 79: 345-349 (1982)), and this naturally occurring sequence can be changed to produce the compound of the present invention. The method of constructing the synthetic gene is known in the technical field of this invention, and reference can be made to, for example, Brown et al.: "Methods in Enzymology", 68: 109-151, Academic Press, NY. A DNA sequence encoding the peptide of the present invention is designed on the basis of the amino acid sequence of the peptide, and DNA having the DNA sequence can be produced by a usual DNA synthesizer such as Model 380A or 380B DNA synthesizer (PE-Applied Biosystems Inc., 850 Lincoln Center Drive, Foster City Calif. 94404).

The DNA used in production of the GLP-1 derivative of the present invention can be devised to increase its expression level and accumulate the product stably in a host, devised to facilitate purification after production, or devised to produce a fusion protein from which the GLP-1 derivative can be easily cut off. For example, such techniques can be exemplified by a technique that involves linking a plurality of genes in tandem each encoding the GLP-1 derivative of the present invention, to increase the expression level, and a technique that involves linking the gene to a gene of protein such as β-galactosidase, β-lactamase, protein A or TrpE to produce the GLP-1 derivative as a fusion protein. In these cases, the GLP-1 derivative can be obtained as its sole peptide after production by previously inserting a gene corresponding to an amino acid methionine into between the respective genes and treating the product with cyan bromide. In this case, the C-terminus of this product is Hse (homoserine). Some GLP-1 derivatives of the present invention have arginine at the C-terminus only, and can be enzymatically treated with arginyl endopeptidase to give the GLP-1 derivative as its sole peptide.

For efficiently expressing the GLP-1 derivative peptide, its synthetic DNA having a predetermined sequence is inserted into a suitable recombinant DNA expression vector by suitable restriction endonuclease. Generally, reference can be made to a literature of Maniatis et al. ("Molecular Cloning", A Laboratory Manual, Vols. 1-3 (1989), Cold Springs Harbor Laboratory Press, NY). To achieve efficient transcription of the synthetic gene, the gene is operatively linked to a promoter/operator region. The synthetic gene promoter/operator region is arranged in the same sequence orientation with respect to the ATG initiation codon of the synthetic gene. Various expression vectors usable in transformation of procaryotic cells and eucaryotic cells are known, and reference can be made to "The Promega Biological Research Products and Catalogue" and "The Stratagene Cloning Systems Catalogue".

After construction of the expression vector for the GLP-1 derivative peptide, the vector is used to transform suitable host cells. As the host cells, either eucaryotic or procaryotic cells can be used. Techniques for transforming the cells are known in this field, and can be found in general literatures such as the above literature of Maniatis et al. Generally, the procaryotic host cells produce a protein in a higher ratio and can be cultured more easily. A protein expressed in a high-level microbial expression system is uniquely aggregated to form particles or inclusion bodies containing the protein expressed in excess at high level. Such typically aggregated protein is solubilized by techniques known in this field, denatured and folded again. For such techniques, reference can be made to "Protein Folding", Kreuger et al. (1990), pp. 136-142, ed. Gierasch and King, American Association for Advancement of Science Publication.

The GLP-1 derivative of the present invention can be combined with a pharmaceutically acceptable carrier, diluent, excipient or absorption promoter to prepare a pharmaceutical composition. The absorption promoter includes, for example, a chelating agent (for example, EDTA, citric acid, salicylate), a surfactant (for example, sodium dodecylsulfate (SDS)), a non-surfactant (for example, unsaturated cyclic urea) and bile acid salts (for example, sodium deoxycholate, sodium taurocholate). Such pharmaceutical compositions can be produced by methods known in the field of pharmaceutical manufacturing. These pharmaceutical preparations are suitable for administration via a mucous membrane in the nasal cavity or the like, and can be used alone or in combination with other therapeutic agents. The GLP-1 derivative of the present invention can also be formed into injections, oral preparations and the like other than the preparation for mucous membrane administration.

Using methods known in the technical field of the present invention, the composition of the present invention can be formed into a preparation to provide continuous or sustained release of the active ingredient immediately after administration into patients. For example, suitable macromolecules (for example, polyester, polyamino acid, polyvinyl pyrrolidone, ethylene vinyl acetate, methyl cellulose, carboxymethyl cellulose and protamine sulfate), or a polymer substance such as polyester, polyamino acid, hydrogel, poly(lactic acid) or ethyl vinyl acetate copolymer can be used to form a complex of the peptide of the present invention or to absorb the peptide of the present invention, in order to produce a preparation showing controlled release. Instead of mixing the peptide with particles of these polymers, the peptide of the present invention can be encapsulated in microcapsules produced by coacervation techniques or interfacial polymerization, microcapsules including hydroxymethyl cellulose or gelatin, in colloidal drug delivery system (for example, liposomes, albumin, microspheres, microemulsion, nano-particles and nano-capsules) or in microemulsion.

In the present invention, a preparation with further improvement in absorption of the peptide of the present invention via mucous membranes can be produced by absorbing the peptide of the present invention onto a charge-regulated fat emulsion prepared according to JP-A 8-27018. As the charge regulator, at least one substance selected from various acidic phospholipids and salts thereof, various fatty acids and salts thereof, bile acids and salts thereof is used. The acidic phospholipids and salts thereof include, but are not limited to, phosphatidyl serine, phosphatidyl glycerol, phosphatidyl inositol, phosphatidic acid and salts thereof. The fatty acids and salts thereof are not particularly limited either, but are preferably C6 or more fatty acids and salts thereof. The bile acids and salts thereof include, but are not limited to, dehydrocholic acid, deoxycholic acid, taurocholic acid and salts thereof. By selecting the charge regulator and establishing the concentration of the charge-regulated fatty emulsion, the pharmaceutical composition of the present invention suitable for administration site can be prepared.

The GLP-1 derivative of the present invention is effective against various diseases against which a GLP-1 preparation is effective. That is, the GLP-1 derivative of the present invention can be used to treat non-insulin dependent mellitus diabetes, insulin-dependent mellitus diabetes, obesity and/or suppression of appetite.

The dose of the GLP-1 derivative of the present invention is determined desirably by those skilled in the art, depending on the respective patients with various diseases. Generally speaking, however, the amount of the GLP-1 derivative to be administered once is considered to be in the range 1 µg/kg to 1 mg/kg, preferably 10 µg/kg to 100 µg/kg. Just before a meal, the GLP-1 derivative is administered once to thrice or more times every day.

Hereinafter, the present invention is described in more detail by reference to Examples and Test Examples. However, these examples are not intended to limit the scope of the present invention.

PRODUCTION EXAMPLE

Synthesis of GLP-1 Derivatives

Synthesis of GLP-1 derivative was conducted by solid phase synthesis with Model 430A Peptide Synthesizer (PE-Applied Biosystems, Foster City, Calif.), and the products were purified by HPLC, and the synthesized products were confirmed by mass spectrometry. The purity of a majority of samples was 95% or more, and such samples were used in in vitro and in vivo tests.

Hereinafter, the synthesized compounds are shown. The sequence of GLP-1 (7-36) is His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Ar g (SEQ ID NO: 2) (that is, GLP-1 (7-36) is the same as GLP-1 (7-35)-Arg). For example, GLP-1 (7-36)+Arg-$NH_2$ is a compound comprising naturally occurring G-GLP-1 (7-36) having one amidated Arg residue added to the C-terminus thereof. Moreover, [$Ser^8$]-GLP-1 (7-35) is a compound wherein Ala at position 2 (corresponding to position 8) was replaced by Ser and the last (corresponding to position 36) Arg was deleted.

Comparative Production Example 1

GLP-1 (7-36)—$NH_2$, which is the Naturally Occurring GLP-1

Comparative Production Example 2: [$Ser^8$]-GLP-1 (7-35)-Arg-$NH_2$ (SEQ ID NO: 3), which is abbreviated to 8S-GLP-1

Production Example 1

GLP-1 (7-36)+Arg-$NH_2$ (SEQ ID NO: 4), which is Abbreviated to GLP-1+1R

Production Example 2

GLP-1 (7-36)+Arg-Arg-$NH_2$ (SEQ ID NO: 5), which is Abbreviated to GLP-1+2R

Production Example 3

[$Ser^8$]-GLP-1 (7-35)-Arg-Arg-Arg-$NH_2$ (SEQ ID NO: 6), which is Abbreviated to 8S-GLP-1+2R Production Example 4

[$Ser^8$]-GLP-1 (7-35)-Arg-Arg-Arg-Arg-$NH_2$ (SEQ ID NO: 7), which is Abbreviated to 8S-GLP-1+3R Production Example 5

[$Ser^8$]-GLP-1 (7-35)-Arg-Arg-Arg-Arg-Arg-$NH_2$ (SEQ ID NO: 8), which is Abbreviated to 8S-GLP-1+4R Production Example 6

[$Ser^8$]-GLP-1 (7-35)-Arg-Arg-Arg-Arg-Arg-Arg-$NH_2$ (SEQ ID NO: 9), which is Abbreviated to 8S-GLP-1+5R Production Example 7

[$Ser^8$]-GLP-1 (7-35)-Arg-Arg-Arg-Arg-Arg-Arg-Arg-$NH_2$ (SEQ ID NO: 10), which is Abbreviated to 8S-GLP-1+6R Production Example 8

[$Ser^8$]-GLP-1 (7-35)-Arg-Arg-Arg-Arg-Arg-Arg-Arg-Arg-Arg-$NH_2$ (SEQ ID NO: 11), which is Abbreviated to 8S-GLP-1+8R Production Example 9

[$Ser^8$]-GLP-1 (7-35)-Lys-Arg-$NH_2$ (SEQ ID NO: 12), which is Abbreviated to 8S, des36R-GLP-1+1KR Production Example 10

[$Ser^8$]-GLP-1 (7-35)-Lys-Lys-Arg-$NH_2$ (SEQ ID NO: 13), which is Abbreviated to 8S, des36R-GLP-1+2KR Production Example 11

[$Ser^8$]-GLP-1 (7-35)-Lys-Lys-Lys-Arg-$NH_2$ (SEQ ID NO: 14), which is Abbreviated to 8S, des36R-GLP-1+3KR Production Example 12

[$Ser^8$]-GLP-1 (7-35)-Lys-Lys-Lys-Lys-Lys-Arg-$NH_2$ (SEQ ID NO: 15), which is Abbreviated to BS, des36R-GLP-1+5KR Production Example 13

[Ser$^8$]-GLP-1 (7-35)-Lys-Lys-Lys-Lys-Lys-Lys-Arg-NH$_2$ (SEQ ID NO: 16), which is Abbreviated to 8S, des36R-GLP-1+7KR Production Example 14

[Ser$^8$]-GLP-1 (7-35)-Lys-Lys-Lys-Lys-Lys-Lys-Lys-Lys-Lys-Arg-NH$_2$ (SEQ ID NO: 17), which is Abbreviated to 8S, des36R-GLP-1+10KR Production Example 15

[Ser$^8$]-GLP-1 (7-35)-Arg-Lys-Lys-NH$_2$ (SEQ ID NO: 18), which is Abbreviated to 8S-GLP-1+2K Reference Production Example 1

[Ser$^8$, Gln$^{26}$, Asn$^{34}$]-GLP-1 (7-35)-Arg (SEQ ID NO: 19), which is Abbreviated to 8S26Q34N-GLP-1

Reference Production Example 2

[Gln$^{26}$, Asn$^{34}$]-GLP-1 (7-35)-Arg-NH$_2$ (SEQ ID NO: 20), which is Abbreviated to 26Q34N-GLP-1

Besides these production examples, GLP-1 derivatives such as Production Example 16, [Ser$^8$, Gln$^{26}$ Asn$^{34}$]-GLP-1 (7-35)-Arg-Arg-Arg-Arg-Arg-NH$_2$ (SEQ ID NO: 21) (abbreviated to 8S26Q34N-GLP-1+4R); Production Example 17, [Ser$^8$, Gln$^{26}$, Asn$^{34}$]-GLP-1 (7-35)-Arg-Arg-Arg-Arg-Arg-Arg-Arg-NH$_2$ (SEQ ID NO: 22) (abbreviated to 8S26Q34N-GLP-1+6R); and Production Example 18, [Ser$^8$ Gln$^{26}$ Asn$^{34}$]-GLP-1 (7-35)-Lys-Lys-Lys-Lys-Lys-Arg-NH$_2$ (SEQ ID NO: 23) (abbreviated to 8S26Q34N, des36R-GLP-1+5KR) are considered preferable.

With respect to Production Examples 1 to 15 and Production Example 16 to 18, the C-terminus is amidated (—NH$_2$), but such derivatives can be non-amidated (—OH) derivatives. For example, the non-amidated (—OH) derivative in Production Example 5 can be made the derivative in Production Example 19, that is, [Ser$^8$]-GLP-1 (7-35)-Arg-Arg-Arg-Arg-Arg (SEQ ID NO: 24) (abbreviated to 8S-GLP-1+4R). The C-terminus can be Hse. Such peptide can be exemplified by the derivative in Production Example 20, that is, [Ser$^8$]-GLP-1 (7-35)-Arg-Arg-Arg-Arg-Hse (SEQ ID NO: 25) (abbreviated to 8S-GLP-1+3RHse).

Test Example 1

Cyclic AMP-Producing Activity of GLP-1 Derivatives

An expression vector of GLP-1 receptor was constructed on the basis of a published DNA sequence of human GLP-1 receptor (Graziano et al., Biochem Biophys Res Com 196: 141-146 (1993)). Chinese hamster ovary CHO-K1 cells were transformed with the vector to give recombinant CHO-K1 cells expressing human GLP-1 receptor.

The human GLP-1 receptor-expressing cells were put at a density of 1×10$^4$ cells/ml/well on a 24-well plate. After 3 days, the cells were used in assay and incubated together with each GLP-1 derivative at 37° C. for 30 minutes in a buffer (PBS, 5.6 mM glucose, 1 mM isobutyl methyl xanthine, 20 μM Ro20-1724, 0.5% BSA, pH 7.4). 10 μl of 5 N hydrochloric acid was added to terminate the incubation.

Cyclic AMP products formed in the cells by the reaction of various GLP-1 derivatives with the GLP-1 receptor were measured by enzyme immunoassays with cAMP-Screen system (Applied Biosystems). The cyclic AMP-producing activities of the various GLP-1 derivatives, in terms of relative activity to that (=100%) of naturally occurring GLP-1, are shown in Table 1.

TABLE 1

Cyclic AMP-producing activities of various GLP-1 derivatives, in terms of relative activity to that (=100%) of naturally occurring GLP-1, in receptor-expressing cells

| GLP-1 derivatives | Concentration of GLP-1 derivative (M) | | |
| --- | --- | --- | --- |
| | $1 \times 10^{-11}$ | $1 \times 10^{-10}$ | $\times 10^{-9}$ |
| GLP-1 | 100.0 | 100.0 | 100.0 |
| GLP-1 + 1R | 7.4 | 100.6 | 78.1 |
| GLP-1 + 2R | 72.3 | 91.9 | 112.4 |
| 8S-GLP-1 | 97.9 | 111.4 | 83.6 |
| 8S-GLP-1 + 2R | 56.4 | 95.5 | 91.2 |
| 8S-GLP-1 + 3R | −17.0 | 75.6 | 101.9 |
| 8S-GLP-1 + 4R | 34.0 | 64.7 | 105.5 |
| 8S-GLP-1 + 5R | 54.3 | 48.6 | 75.6 |
| 8S-GLP-1 + 6R | 64.9 | 81.1 | 80.6 |
| 8S-GLP-1 + 8R | 74.5 | 87.4 | 95.9 |
| 8S, des36R-GLP-1 + 1KR | 100.1 | 112.9 | 80.5 |
| 8S, des36R-GLP-1 + 2KR | 36.2 | 88.9 | 81.6 |
| 8S, des36R-GLP-1 + 3KR | 45.0 | 96.6 | 86.7 |
| 8S, des36R-GLP-1 + 5KR | 7.9 | 55.3 | 63.4 |
| 8S, des36R-GLP-1 + 7KR | 8.8 | 55.6 | 92.6 |
| 8S, des36R-GLP-1 + 10KR | 7.5 | 20.8 | 55.4 |
| 8S-GLP-1 + 2K | 53.2 | 103.8 | 88.8 |

As a result, any GLP-1 derivatives had an in vitro activity of producing cyclic AMP. However, there was a tendency for the activity to be decreased as the number of arginine or lysine residues added was increased. This tendency was recognized particularly with respect to lysine. However, it is highly possible that the added arginine or lysine residues will be cleaved by peptidase upon absorption via a mucous membrane, and thus this in vitro activity does not necessarily reflect the in vivo activity, and this in consistence may bring about results in in vivo tests described below.

Test Example 2

Blood Glucose Lowering Activity and Insulin Secretion Stimulating Activity of GLP-1 Derivatives Absorbed Via Mucous Membrane An increase in absorption of the GLP-1 derivative via a mucous membrane was evaluated in terms of in vivo blood glucose lowering activity and insulin secretion stimulating activity. That is, the GLP-1 derivative was administered via the nose into mice, and evaluated in an oral glucose tolerance test (OGTT) where a change in blood glucose level in the mice after tolerated with glucose was measured.

The GLP-1 derivative was dissolved in distilled water to give 1 mM solution which was then stocked at −80° C. At the time of the test, the solution was diluted to a predetermined concentration with physiological saline.

Mice were anesthetized lightly with ether. 20 μl GLP-1 derivative solution was taken in a micropipette and discharged through the tip of the micropipette into the nose of each mouse. The GLP-1 derivative solution was inhaled by breathing through the nose into the mouse. Five minutes after the nasal administration of GLP-1 derivative, 5% glucose solution was orally administered through a probe in an amount of 10 ml/kg.

The blood glucose level was determined by collecting several μl blood from a cut in the tail just before the test and 5, 10 and 20 minutes after glucose administration, and measuring the blood with a small blood-glucose-level measuring instrument (Glutest Ace, manufactured by Sanwa Kagaku Kenkyusho Co., Ltd.). The area under the blood concentration-time curve (AUC 0-20 min) as an increase from the blood glucose level in each mouse before administration of the GLP-1 derivative was calculated.

The blood insulin level was determined by collecting 75 μl blood from an orbital venous plexus with a heparin-treated glass capillary 5 minutes after administration of glucose, then centrifuging the blood and measuring plasma insulin by EIA (Levis Mouse Insulin Kit, manufactured by Shibayagi Co., Ltd.).

The blood glucose level and blood insulin level in the group given GLP-1 derivatives, expressed in terms of average and standard error, are shown in Table 2.

TABLE 2

Blood glucose level and blood insulin level upon administration of GLP-1 derivative in OGTT test

| Administered sample | Dose (nmol/ mouse) | Blood glucose level (area under blood concentration-time curve ($AUC_{0\text{-}20\ min}$) (mg/dl · min) | Blood insulin level (5 minutes after glucose administration (ng/mL) |
|---|---|---|---|
| Physiological saline | 0 | 712 ± 103 | 632 ± 107 |
| Naturally occurring GLP-1 | 1.07 | 697 ± 94 | 662 ± 91 |
| Naturally occurring GLP-1 | 10.7 | 399 ± 35 | 743 ± 147 |
| 8S-GLP-1 | 1.07 | 624 ± 89 | 1026 ± 199 |
| 8S-GLP-1 | 10.7 | 291 ± 66 | 1289 ± 165 |
| 8S-GLP-1 + 2R | 1.07 | 535 ± 58 | 957 ± 86 |
| 8S-GLP-1 + 3R | 1.07 | 509 ± 92 | 1359 ± 318 |
| 8S-GLP-1 + 4R | 1.07 | 388 ± 54 | 1713 ± 430 |
| 8S-GLP-1 + 5R | 1.07 | 483 ± 26 | 1504 ± 250 |
| 8S-GLP-1 + 6R | 1.07 | 559 ± 27 | 1633 ± 449 |
| 8S-GLP-1 + 8R | 1.07 | 487 ± 32 | 1882 ± 402 |
| 8S, des36R-GLP-1 + 1KR | 1.07 | 611 ± 51 | 1349 ± 244 |
| 8S, des36R-GLP-1 + 2KR | 1.07 | 564 ± 52 | 1243 ± 309 |
| 8S, des36R-GLP-1 + 3KR | 1.07 | 557 ± 53 | 1176 ± 233 |
| 8S, des36R-GLP-1 + 5KR | 1.07 | 404 ± 71 | 2229 ± 346 |
| 8S, des36R-GLP-1 + 7KR | 1.07 | 457 ± 69 | 1604 ± 344 |
| 8S, des36R-GLP-1 + 10KR | 1.07 | 492 ± 106 | 2379 ± 520 |
| 8S-GLP-1 + 2K | 1.07 | 598 ± 63 | 862 ± 150 |

As a result, it was found that GLP-1 derivatives 8S-GLP-1+4R and 8S, des36R-GLP-1+5KR exhibited the strongest blood glucose depressing action. The derivatives having arginine residues added to 8S-GLP-1+4R or more or the derivatives having lysine residues added to 8S, des36R-GLP-1+5KR or more exhibited the strongest insulin secretion stimulating activity. These derivatives in an amount of 1/10 relative to naturally occurring GLP-1 showed a similar effect to that of the naturally occurring one, and thus the absorption of these GLP-1 derivatives was considered to be 10 times as high as that of the naturally occurring GLP-1.

Test Example 3

Action of Charge-Regulated Fat Emulsion on Absorption of GLP-1 Derivatives Via Mucous Membrane The blood glucose lowering activity and insulin secretion stimulating activity of GLP-1 derivatives used in combination with the charge-regulated fat emulsion were examined in an oral glucose tolerance test conducted in the same manner as in Text Example 2. The charge-regulated fat emulsion used was prepared according to JP-A 8-27018; that is, a charge-regulated fat emulsion at a final concentration of 8% was obtained by using 2% (w/w) phosphatidyl glycerol (sodium salt), 8% (w/w) neutral oil and 90% (w/w) water.

50 μl of 8% charge-regulated fat emulsion was mixed with 3.56 μl of 1 mM 8S-GLP-1+5R solution and 146.4 μl distilled water to give 2% charge-regulated fat emulsion solution containing 8S-GLP-1+5R at a final concentration of 0.0178 mM. As controls for comparison, 0.534 mM naturally occurring GLP-1 solution (whose concentration is 30 times as high as that of 8S-GLP-1+5R) not containing 2% charge-regulated fat emulsion, 0.0178 mM 8S-GLP-1+5R solution not containing 2% charge-regulated fat emulsion, and physiological saline were used respectively.

Mice were anesthetized lightly with ether. 20 μl GLP-1 derivative solution was taken in a micropipette and discharged through the tip of the micropipette into the nose of each mouse. The GLP-1 derivative solution was inhaled by breathing through the nose into the mouse. Five minutes after the nasal administration of GLP-1 derivative, 5% glucose solution was orally administered through a probe in an amount of 10 ml/kg.

The blood glucose level was determined by collecting several μl blood from a cut in the tail just before the test and 10, 20 and 30 minutes after glucose administration, and measuring glucose with a blood-glucose-level measuring instrument (Glutest Ace, manufactured by Sanwa Kagaku Kenkyusho Co., Ltd.). The area under the blood concentration-time curve (AUC 0-30 min) as an increase from the blood glucose level in each mouse before administration of the GLP-1 derivative was calculated.

The blood insulin level was determined by collecting 75 μl blood from an orbital venous plexus with a heparin-treated glass capillary 10 minutes after administration of glucose, then centrifuging the blood and measuring plasma insulin by EIA (Levis Mouse Insulin Kit, manufactured by Shibayagi Co., Ltd.).

The blood glucose level and blood insulin level in the group given GLP-1 derivatives, expressed in terms of average and standard error, are shown in Table 3.

TABLE 3

Blood glucose level and blood insulin level in OGTT test upon administration of GLP-1 derivatives used in combination with charge-regulated fat emulsion

| Administered sample | Dose (nmol/ mouse) | Blood glucose level (area under blood concentration-time curve ($AUC_{0\text{-}30\ min}$) (ng/dl · min) | Blood insulin level (10 minutes after glucose administration) (ng/mL) |
|---|---|---|---|
| Physiological saline | 0 | 2122 ± 198 | 251 ± 12 |
| Naturally occurring GLP-1 | 10.7 | 1533 ± 111 | 377 ± 41 |

TABLE 3-continued

Blood glucose level and blood insulin level in OGTT test upon administration of GLP-1 derivatives used in combination with charge-regulated fat emulsion

| Administered sample | Dose (nmol/mouse) | Blood glucose level (area under blood concentration-time curve ($AUC_{0-30\ min}$) (ng/dl · min) | Blood insulin level (10 minutes after glucose administration) (ng/mL) |
|---|---|---|---|
| 8S-GLP-1 + 5R Used in combination with charge-regulated fat emulsion | 0.357 | 2025 ± 176 | 506 ± 34 |
| 8S-GLP-1 + 5R | 0.357 | 1526 ± 354 | 560 ± 81 |

As a result, 8S-GLP-1+5R used in combination with the charge-regulated fat emulsion, in an amount of 1/30 relative to the naturally occurring GLP-1 without charge-regulated fat emulsion, exhibited a similar blood glucose lowering activity similar to that of the naturally occurring GLP-1. That is, the effect of 8S-GLP-1+5R was exhibited at a lower concentration thereof by using the charge-regulated fat emulsion.

Test Example 4

Evaluation of Activity of GLP-1 Derivative 8S26Q34N-GLP-1

The in vitro activity of GLP-1 derivative 8S26Q34N-GLP-1 in producing cyclic AMP was measured according to the method in Test Example 1. After amino acid substitution, the activity was maintained as well (Table 4).

TABLE 4

Cyclic AMP producing activity of 8S26Q34N-GLP-1

| Concentration of 8S26Q34N-GLP-1 (log M) | Amount of cAMP produced (pmol/$10^5$ cell/30 min) |
|---|---|
| −12 | 0.6 |
| −11 | 4.7 |
| −10 | 24.2 |
| −9 | 76.1 |
| −8 | 79.2 |

When the insulin secretion stimulating activity was examined for 30 minutes in the presence of 16.7 mM glucose (high blood glucose condition) by using mouse Langerhans islet, the GLP-1 derivative S26Q34N-GLP-1 showed a stronger insulin secretion stimulating activity than that of the naturally occurring GLP-1 (Table 5).

TABLE 5

Insulin secretion stimulating activity of 8S26Q34N-GLP-1 in the presence of 16.7 mM glucose by using mouse Langerhans islet

| Assay concentration (log M) | Amount of insulin secreted (ng/islet/30 min) | |
|---|---|---|
| | Naturally occurring GLP-1 | 8S26Q34N-GLP-1 |
| 0 | | 2.61 |
| −10 | 4.11 | 3.64 |

TABLE 5-continued

Insulin secretion stimulating activity of 8S26Q34N-GLP-1 in the presence of 16.7 mM glucose by using mouse Langerhans islet

| Assay concentration (log M) | Amount of insulin secreted (ng/islet/30 min) | |
|---|---|---|
| | Naturally occurring GLP-1 | 8S26Q34N-GLP-1 |
| −9 | 5.11 | 6.61 |
| −8 | 6.71 | 9.85 |

The blood glucose lowering activity in mice was examined by administering the GLP-1 derivative subcutaneously into mice, and 0.5 g/kg glucose administered through a tail vain into mice 5 minutes after administration of the GLP-1 derivative. The GLP-1 derivative 8S26Q34N-GLP-1 showed concentration-dependent depression in blood glucose level, and this activity was stronger than that of the naturally occurring GLP-1 (Table 6)

TABLE 6

Activity of 8S26Q34N-GLP-1 derivative on blood glucose level in mouse

| Dose (μg/kg) | Blood sugar level 20 minutes after tolerance with glucose (mg/dl) | |
|---|---|---|
| | Naturally occurring GLP-1 | 8S26Q34N-GLP-1 |
| 0 | 123 | |
| 5 | 119 | 110 |
| 10 | 103 | 95 |
| 20 | 75 | 21 |

The results of this test indicate that the GLP-1 derivative in Reference Production Example 1 maintains a GLP-1 activity. When the test results in Table 1 are also taken into consideration, it can be concluded that even if several residues of arginine and/or lysine are added to the C-terminus of this GLP-1 derivative, its GLP-1 activity can be still maintained.

Test Example 5

Evaluation of Resistance of GLP-1 Derivative 8S-GLP-1 to Dipeptidyl Peptidase IV (DPPIV)

500 μM GLP-1 derivative 8S-GLP-1 was mixed with 40 μU/μl dipeptidyl peptidase IV and incubated at 37° C. for 60 minutes. Thereafter, the sample was extracted with a 2-fold excess volume of ethanol, centrifuged and evaporated into dryness by an evaporator. The resulting dried product was dissolved in distilled water containing 1% BSA, and its cyclic AMP production activity was measured according to Test Example 1, to calculate the residual activity (%).

As a result, there was no difference in activity of the derivative regardless of whether it was treated or not treated with dipeptidyl peptidase IV, thus indicating that this GLP-1 derivative is resistant to dipeptidyl peptidase IV. Accordingly, the GLP-1 derivative can acquire resistance to dipeptidyl peptidase IV by substituting position 8 with serine (Table 7).

TABLE 7

| Peptide | Residual activity (%) DPP IV | |
|---|---|---|
| | − | + |
| 8S-GLP-1 | 100% | 101% |
| Naturally occurring GLP-1 | 100% | 25% |

Test Example 6

Evaluation of Resistance of GLP-1 Derivative 26Q34N-GLP-1 to Trypsin

The GLP-1 derivative 26Q34N-GLP-1 in Reference Production Example 2 was dissolved at a concentration of 500 µg/ml in 50 mM ammonium bicarbonate at pH 7.8. Then, 5 µl of 500 µg/ml trypsin (Promega Cat. No. V5113) was added to 100 µl of the solution, and the mixture was incubated at 37° C. for 1 hour. The reaction was terminated by adding 1200 µl of 71.5% (final 65%) ethanol, and the reaction solution was centrifuged at 15,000 rpm at 4° C. for 5 minutes to recover a supernatant which was then evaporated into dryness. The dried product was dissolved in distilled water and measured for cAMP activity by the method in Test Example 1, to determine the residual activity (%).

As a result, there was no difference in activity of the derivative regardless of whether it was treated or not treated with trypsin, thus indicating that this GLP-1 derivative is resistant to trypsin (Table 8).

TABLE 8

| Peptide | Residual activity (%) Trypsin | |
|---|---|---|
| | − | + |
| 26Q34N-GLP-1 | 100% | 94.8% |

This result indicates that the GLP-1 derivative is rendered resistant to trypsin by substituting amino acids at positions 26 and 34 in the GLP-1 derivative with glutamine and asparagine, respectively. Thus, it can be concluded that GLP-1 derivatives having several residues of arginine and/or lysine added to the C-terminus thereof also have resistance to trypsin.

INDUSTRIAL APPLICABILITY

Clinical application of GLP-1 by subcutaneous injection is advancing at present. This is because GLP-1 is a peptide which cannot be absorbed upon oral administration. The product of the present invention solves this problem and enables administration in a form other than injection. Because treatment of diabetes by using GLP-1 will last for a long time, the treatment without repeated injection is greatly advantageous to the patients.

SEQUENCE LISTING

```
<160> NUMBER OF SEQ ID NOS: 25

<210> SEQ ID NO 1
<211> LENGTH: 29
<212> TYPE: PRT
<213> ORGANISM: Artificial
<220> FEATURE:
<223> OTHER INFORMATION: GLP1(7-35)

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly
            20                  25

<210> SEQ ID NO 2
<211> LENGTH: 30
<212> TYPE: PRT
<213> ORGANISM: Artificial
<220> FEATURE:
<223> OTHER INFORMATION: GLP1(7-36)

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 3
<211> LENGTH: 30
```

```
<212> TYPE: PRT
<213> ORGANISM: Artificial
<220> FEATURE:
<223> OTHER INFORMATION: 8S-GLP1

<400> SEQUENCE: 3

His Ser Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30

<210> SEQ ID NO 4
<211> LENGTH: 31
<212> TYPE: PRT
<213> ORGANISM: Artificial
<220> FEATURE:
<223> OTHER INFORMATION: GLP1+1R

<400> SEQUENCE: 4

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Arg
            20                  25                  30

<210> SEQ ID NO 5
<211> LENGTH: 32
<212> TYPE: PRT
<213> ORGANISM: Artificial
<220> FEATURE:
<223> OTHER INFORMATION: GLP1+2R

<400> SEQUENCE: 5

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Arg Arg
            20                  25                  30

<210> SEQ ID NO 6
<211> LENGTH: 32
<212> TYPE: PRT
<213> ORGANISM: Artificial
<220> FEATURE:
<223> OTHER INFORMATION: 8S-GLP1+2R

<400> SEQUENCE: 6

His Ser Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Arg Arg
            20                  25                  30

<210> SEQ ID NO 7
<211> LENGTH: 33
<212> TYPE: PRT
<213> ORGANISM: Artificial
<220> FEATURE:
<223> OTHER INFORMATION: 8S-GLP1+3R

<400> SEQUENCE: 7

His Ser Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Arg Arg
            20                  25                  30

Arg
```

<210> SEQ ID NO 8
<211> LENGTH: 34
<212> TYPE: PRT
<213> ORGANISM: Artificial
<220> FEATURE:
<223> OTHER INFORMATION: 8S-GLP1-4R

<400> SEQUENCE: 8

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Arg Arg
            20                  25                  30

Arg Arg

<210> SEQ ID NO 9
<211> LENGTH: 35
<212> TYPE: PRT
<213> ORGANISM: Artificial
<220> FEATURE:
<223> OTHER INFORMATION: 8S-GLP1+5R

<400> SEQUENCE: 9

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Arg Arg
            20                  25                  30

Arg Arg Arg
        35

<210> SEQ ID NO 10
<211> LENGTH: 36
<212> TYPE: PRT
<213> ORGANISM: Artificial
<220> FEATURE:
<223> OTHER INFORMATION: 8S-GLP1+6R

<400> SEQUENCE: 10

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Arg Arg
            20                  25                  30

Arg Arg Arg Arg
        35

<210> SEQ ID NO 11
<211> LENGTH: 38
<212> TYPE: PRT
<213> ORGANISM: Artificial
<220> FEATURE:
<223> OTHER INFORMATION: 8S-GLP1-8R

<400> SEQUENCE: 11

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Arg Arg
            20                  25                  30

Arg Arg Arg Arg Arg Arg
        35

<210> SEQ ID NO 12
<211> LENGTH: 31
<212> TYPE: PRT

-continued

```
<213> ORGANISM: Artificial
<220> FEATURE:
<223> OTHER INFORMATION: 8S-des36R-GLP1+1KR

<400> SEQUENCE: 12

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Lys Arg
            20                  25                  30

<210> SEQ ID NO 13
<211> LENGTH: 32
<212> TYPE: PRT
<213> ORGANISM: Artificial
<220> FEATURE:
<223> OTHER INFORMATION: 8S-des36R-GLP1+2KR

<400> SEQUENCE: 13

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Lys Lys Arg
            20                  25                  30

<210> SEQ ID NO 14
<211> LENGTH: 33
<212> TYPE: PRT
<213> ORGANISM: Artificial
<220> FEATURE:
<223> OTHER INFORMATION: 8S-des36R-GLP1+3KR

<400> SEQUENCE: 14

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Lys Lys Lys
            20                  25                  30

Arg

<210> SEQ ID NO 15
<211> LENGTH: 35
<212> TYPE: PRT
<213> ORGANISM: Artificial
<220> FEATURE:
<223> OTHER INFORMATION: 8S-des36R-GLP1+5KR

<400> SEQUENCE: 15

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Lys Lys Lys
            20                  25                  30

Lys Lys Arg
        35

<210> SEQ ID NO 16
<211> LENGTH: 37
<212> TYPE: PRT
<213> ORGANISM: Artificial
<220> FEATURE:
<223> OTHER INFORMATION: 8S-des36R-GLP1+7KR

<400> SEQUENCE: 16

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Lys Lys Lys
```

```
                20                  25                  30

Lys Lys Lys Lys Arg
        35

<210> SEQ ID NO 17
<211> LENGTH: 40
<212> TYPE: PRT
<213> ORGANISM: Artificial
<220> FEATURE:
<223> OTHER INFORMATION: 8S-des36R-GLP1+10KR

<400> SEQUENCE: 17

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Lys Lys Lys
            20                  25                  30

Lys Lys Lys Lys Lys Lys Lys Arg
        35                  40

<210> SEQ ID NO 18
<211> LENGTH: 32
<212> TYPE: PRT
<213> ORGANISM: Artificial
<220> FEATURE:
<223> OTHER INFORMATION: 8S-GLP1+2K

<400> SEQUENCE: 18

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Lys Lys
            20                  25                  30

<210> SEQ ID NO 19
<211> LENGTH: 30
<212> TYPE: PRT
<213> ORGANISM: Artificial
<220> FEATURE:
<223> OTHER INFORMATION: 8S26Q34N-GLP1

<400> SEQUENCE: 19

His Ser Glu Gly Thr Phe Thr Ser Asp Val Ser Ser Tyr Leu Glu Gly
1               5                   10                  15

Gln Ala Ala Gln Glu Phe Ile Ala Trp Leu Val Asn Gly Arg
            20                  25                  30

<210> SEQ ID NO 20
<211> LENGTH: 30
<212> TYPE: PRT
<213> ORGANISM: Artificial
<220> FEATURE:
<223> OTHER INFORMATION: 26Q34N-GLP1

<400> SEQUENCE: 20

His Ala Glu Gly Thr Phe Thr Ser Asp Val Ser Ser Tyr Leu Glu Gly
1               5                   10                  15

Gln Ala Ala Gln Glu Phe Ile Ala Trp Leu Val Asn Gly Arg
            20                  25                  30

<210> SEQ ID NO 21
<211> LENGTH: 34
<212> TYPE: PRT
<213> ORGANISM: Artificial
<220> FEATURE:
<223> OTHER INFORMATION: 8S26Q34N-GLP1+4R
```

<400> SEQUENCE: 21

His Ser Glu Gly Thr Phe Thr Ser Asp Val Ser Ser Tyr Leu Glu Gly
1               5                   10                  15

Gln Ala Ala Gln Glu Phe Ile Ala Trp Leu Val Asn Gly Arg Arg Arg
            20                  25                  30

Arg Arg

<210> SEQ ID NO 22
<211> LENGTH: 36
<212> TYPE: PRT
<213> ORGANISM: Artificial
<220> FEATURE:
<223> OTHER INFORMATION: 8S26Q34N-GLP1-6R

<400> SEQUENCE: 22

His Ser Glu Gly Thr Phe Thr Ser Asp Val Ser Ser Tyr Leu Glu Gly
1               5                   10                  15

Gln Ala Ala Gln Glu Phe Ile Ala Trp Leu Val Asn Gly Arg Arg Arg
            20                  25                  30

Arg Arg Arg Arg
        35

<210> SEQ ID NO 23
<211> LENGTH: 35
<212> TYPE: PRT
<213> ORGANISM: Artificial
<220> FEATURE:
<223> OTHER INFORMATION: 8S26Q34N-des36R-GLP1-5KR

<400> SEQUENCE: 23

His Ser Glu Gly Thr Phe Thr Ser Asp Val Ser Ser Tyr Leu Glu Gly
1               5                   10                  15

Gln Ala Ala Gln Glu Phe Ile Ala Trp Leu Val Asn Gly Lys Lys Lys
            20                  25                  30

Lys Lys Arg
        35

<210> SEQ ID NO 24
<211> LENGTH: 34
<212> TYPE: PRT
<213> ORGANISM: Artificial
<220> FEATURE:
<223> OTHER INFORMATION: 8S-GLP1-4R

<400> SEQUENCE: 24

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Arg Arg
            20                  25                  30

Arg Arg

<210> SEQ ID NO 25
<211> LENGTH: 34
<212> TYPE: PRT
<213> ORGANISM: Artificial
<220> FEATURE:
<223> OTHER INFORMATION: 8S-GLP1+3RHse
<220> FEATURE:
<221> NAME/KEY: misc_feature
<222> LOCATION: (34)..(34)
<223> OTHER INFORMATION: Xaa is Homoserine.

```
<400> SEQUENCE: 25

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Arg Arg
            20                  25                  30

Arg Xaa
1/18
```

The invention claimed is:

1. A peptide having a formula of GLP-1 Waa-(xaa)n-Yaa, said peptide consisting of a GLP-1 peptide, Waa connected to the GLP-1 peptide at the C-terminus of the GLP-1 peptide, (Xaa)n connected to Waa, and Yaa connected to (Xaa)n (in which Waa is Arg or Lys, Xaa is Lys, n is an integer of 1 to 9, and Yaa is Arg or Arg-NH$_2$), wherein the GLP-1 peptide is selected from the group consisting of GLP-1(7-35), [Ser$^8$]-GLP-1(7-35), [Gln$^{26}$, Asn$^{34}$]-GLP-1(7-35), and [Ser$^8$, Gln$^{26}$, Asn$^{34}$]-GLP-1(7-35).

2. The peptide according to claim 1, wherein the GLP-1 peptide is [Ser$^8$]-GLP-1(7-35).

3. The peptide according to claim 1, wherein the GLP-1 peptide is [Gln$^{26}$, Asn$^{34}$]-GLP-1(7-35).

4. The peptide according to claim 1, wherein the GLP-1 peptide is [Ser$^8$, Gln$^{26}$, Asn$^{34}$]-GLP-1(7-35).

5. The peptide according to claim 1, wherein n is an integer of 3 to 5.

6. The peptide according to claim 1, which has a higher efficiency of transmucosal absorption than that of naturally occurring GLP-1.

7. A pharmaceutical composition for transmucosal administration containing as an active ingredient a peptide having a formula of GLP-1-Waa-(xaa)n-Yaa, said peptide consisting of a GLP-1 peptide, Waa connected to the (GLP-1 peptide at the C-terminus of the GLP-1 peptide (Xaa)n connected to Waa, and Yaa connected to (Xaa)n (in which Waa is Arg or Lys, Xaa is Lys, n is an integer of 1 to 9, and Yaa is Arg or Arg-NH$_2$), wherein the GLP-1 peptide is selected from the group consisting of GLP-1(7-35), [Ser$^8$]-GLP-1(7-35). [Gln$^{26}$, Asn$^{34}$]-GLP-1(7-35), and [Ser$^8$, Gln$^{26}$, Asn$^{34}$]-GLP-1(7-35).

8. The pharmaceutical composition according to claim 7, which is used for nasal administration.

9. The pharmaceutical composition according to claim 7, which is used in treatment of non-insulin dependent chronic diabetes mellitus, treatment of insulin dependent chronic diabetes mellitus, treatment of obesity and/or suppression of appetite.

10. The pharmaceutical composition according to claim 7, wherein the GLP-1 peptide is [Ser$^8$]-GLP-1(7-35).

11. The pharmaceutical composition according to claim 7, wherein the GLP-1 peptide is [Gln$^{26}$, Asn$^{34}$]-GLP-1(7-35).

12. The pharmaceutical composition according to claim 7, wherein the GLP-1 peptide is [Ser$^8$,Gln$^{26}$, Asn$^{34}$]-GLP-1(7-35).

13. A method for treating non-insulin dependent diabetes muellitus, insulin dependent diabetes mellitus and/or obesity which comprises transmucosally administering to the patient a pharmaceutical composition containing as an active ingredient a peptide having a formula of GLP-1-Waa-(xaa)n-Yaa, said peptide consisting of a GLP-1 peptide, Waa connected to the GLP-1 peptide at the C-terminus of the GLP-1 peptide, (Xaa)n connected to Waa, and Yaa connected to (Xaa)n (in which Waa is Arg or Lys, Xaa is Lys, n is an integer of 1 to 9, and Yaa is Arg or Arg-NH$_2$), wherein the GLP-1 peptide is selected from the group consisting of GLP-1(7-35), [Ser$^8$]-GLP-1(7-35), [Gln$^{26}$, Asn$^{34}$]-GLP-1(7-35), and [Ser$^8$, Gln$^{26}$, Asn$^{34}$]-GLP-1(7-35).

14. The method according to claim 13, wherein the GLP-1 peptide constituting the active ingredient of the pharmaceutical composition is [Ser$^8$]-GLP-1(7-35).

15. The method according to claim 13, wherein the GLP-1 peptide constituting the active ingredient of the pharmaceutical composition is [Gln$^{26}$, Asn$^{34}$]-GLP-1(7-35).

16. The method according to claim 13, wherein the GLP-1 peptide constituting the active ingredient of the pharmaceutical composition is [Ser$^8$, Gln$^{26}$, Asn$^{34}$]-GLP-1(7-35).

* * * * *